United States Patent [19]

Fridlender

[11] 4,313,927
[45] Feb. 2, 1982

[54] IMMUNOASSAY METHOD FOR DETECTING VIRAL ANTIBODIES IN WHOLE BLOOD SAMPLES

[75] Inventor: Bertold R. Fridlender, Jerusalem, Israel

[73] Assignee: Ames-Yissum Ltd., Jerusalem, Israel

[21] Appl. No.: 86,399

[22] Filed: Oct. 19, 1979

[51] Int. Cl.³ .................. G01N 33/56; G01N 33/58
[52] U.S. Cl. ................................. 424/1; 23/230 B; 424/8; 424/12; 435/7
[58] Field of Search .............. 424/1, 12, 8; 23/230 B; 435/7

[56] References Cited

U.S. PATENT DOCUMENTS 4,178,360 12/1979 Cleeland et al. .................. 424/1
4,185,084 1/1980 Mochida et al. .................. 424/1

*Primary Examiner*—Christine M. Nucker
*Attorney, Agent, or Firm*—Andrew L. Klawitter

[57] ABSTRACT

An immunoassay method for the detection of an antibody ($Ab_1$) to a viral antigen (Ag) wherein a whole human blood sample diluted with an isotonic aqueous solution is incubated with a solid-phase form of Ag whereby any $Ab_1$ present in the sample becomes bound to solid-phase Ag, the resulting solid-phase Ag-$Ab_1$ complexes are separated from the sample, a label-incorporated form of an antibody to $Ab_1$ ($Ab_2^*$) is contacted with the separated, solid-phase Ag-$Ab_1$ complexes, the resulting solid-phase Ag-$Ab_1$-$Ab_2^*$ complexes are separated from excess $Ab_2^*$, and the amount of the label in the separated, solid-phase Ag-$Ab_1Ab_2^*$ complexes is measured as a function of the presence of $Ab_1$ in the sample. Preferably the whole blood sample is diluted 1:20 by volume with an isotonic aqueous buffer solution. The method is particularly useful for the detection of cytomegalovirus antibody or Rubella antibody.

11 Claims, No Drawings

IMMUNOASSAY METHOD FOR DETECTING VIRAL ANTIBODIES IN WHOLE BLOOD SAMPLES

BACKGROUND OF THE INVENTION

1. Field of the Invention

This invention relates to immunoassay methods for detecting the presence of antibodies to viral antigens in test samples derived from human blood. The detection of viral antibodies in a patient's blood is indicative of past or current viral infection. Such information can be of great clinical value, particularly in prenatal screens to determine risks from infections due to such viral agents as cytomegalovirus, Rubella virus, herpesvirus, and the like or to determine success obtained with vaccinations against viral diseases such as measles, Rubella, mumps, polio and the like.

It is evident that a most desirable feature of any clinical assay is the ability to perform the assay on an easily obtainable sample with a minimum of sample pretreatment. Where the object of an assay is a component of blood, obviously the most desirable assay sample would be whole (or untreated) blood. However, as demonstrated below, the previously known immunoassays for viral antibodies have consistently been limited to assaying treated blood samples, primarily serum. Procedures for obtaining serum samples from whole blood samples require the use of apparatus and the skills of a technician, both of which add to assay time and cost. It has been discovered that, contrary to the prejudices raised by the prior art, the present immunoassay method can be used to assay whole human blood samples.

2. Brief Description of the Prior Art

Over the years, several different techniques have evolved for the determination of viral antibodies including complement fixation, hemagglutination, and, more recently, various immunoassays such as radioimmunoassay and enzyme immunoassay. Under the current state of the art, the method of choice is an immunoassay technique referred to as the indirect, solid-phase immunoassay.

In such a method for detecting an antibody to a viral antigen (hereinafter such antibody being abbreviated as "$Ab_1$" and such antigen as "Ag"), a test sample, such as serum, derived from human blood is incubated with a solid-phase (i.e., immobilized or insolubilized) form of Ag whereby any $Ab_1$ present in the test sample becomes bound to the solid-phase Ag. After this first incubation, the resulting solid-phase Ag-$Ab_1$ complexes are separated from the test sample and a label-incorporated form of an antibody to $Ab_1$ (such labeled antibody being abbreviated as "$Ab_2$*") is contacted with the separated, solid-phase Ag-$Ab_1$ complexes. Where the label is radioactive, the assay is known as a radioimmunoassay. Other, nonradioisotopic, techniques can also be used. Where the label is an enzyme, the assay is known as an enzyme immunoassay.

After a second incubation period, the resulting solid-phase Ag-$Ab_1$-$Ab_2$* complexes are separated from excess $Ab_2$*. Then, the amount of the label in the separated, solid-phase Ag-$Ab_1$-$Ab_2$* complexes is measured and is a function of the presence or amount of $Ab_1$ in the test sample. If a significant amount of $Ab_1$ is present in the sample, it will become bound to solid-phase Ag and thereafter by $Ab_2$* so that the association of the label with the solid-phase in significant amounts is due to the presence of $Ab_1$.

This indirect, solid-phase immunoassay technique can be schematically illustrated as follows:

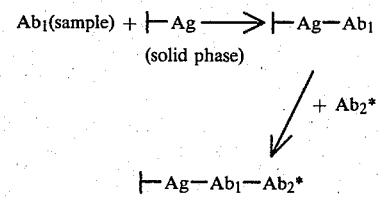

Representative of the known indirect, solid-phase immunoassays for viral antibodies are the procedures described in the following references: for the detection of antibodies to cytomegalovirus—*Archives of Virology* 58: 253 (1978), *J. Immunol.* 117: 2006 (1976), *Brit. J. Exp. Pathol.* 57: 243 (1976), and *J. Infect. Dis.* 136 Suppl. 5337 (1977) and for the detection of antibodies to Rubella—*Brit. J. Exp. Pathol.* 56: 338 (1975), *J. Clin. Microbiol.* 4: 117 (1976), *Infection and Immunity* 19: 369 (1978), *Acta Path. and Microbiol. Scan.* Section B 85: 113 (1977), *Clin. and Exp. Immunol.* 31: 50 (1978), and *Res. Comm. Chem. Pathol. and Pharm.* 19: 281 (1978). All of the above described techniques are directed specifically and solely to the assay of serum. Such references further reinforce the prejudice against performing the involved immunoassays on whole, untreated blood samples, a course of action which would clearly be more advantageous in terms of cost, convenience, simplicity and assay time.

SUMMARY OF THE INVENTION

It has now been discovered that the prior art indirect, solid-phase immunoassays for detecting viral antibodies can be applied directly to whole human blood samples. The qualitative and quantitative results using whole blood samples are virtually the same as those using serum samples as required by the prior art. In accordance with the present invention, the test sample employed in the assay is whole human blood diluted at least 1:20 by volume with an isotonic (i.e., having the same osmotic pressure as human blood) aqueous solution. Whole blood samples can be obtained by a simple finger prick or by conventional venipuncture and the assay run on the diluted sample without removal of red blood cells. The present assay is particularly applicable to the detection of antibodies to cytomegalovirus and/or Rubella antigens. Antibodies of various immune globulin classes, including IgG and IgM particularly, can be detected. Any conventional label may be used, including radioactive and enzyme labels.

DESCRIPTION OF THE PREFERRED EMBODIMENTS

It has been unexpectedly found that the prejudices raised by the prior art against the immunoassay of whole blood samples are without substance, that the presence of red blood cells in the test sample (which cells are not present in sera) has no significant effect on the qualitative or quantitative assay results. Virtually identical correlation of assay results between serum and whole blood samples is attainable by diluting the whole blood samples by a predetermined factor, usually 2, to compensate for the volume of red blood cells in whole blood samples compared to plasma.

The test sample to be assayed is prepared by diluting whole blood by at least a factor of 1:20 by volume with the isotonic aqueous solution. Lesser dilutions have been found not to yield reproducible assay results due to high background levels of the label. Greater dilutions are possible with attendant loss in sensitivity at excessively high dilutions. A dilution of 1:50 by volume has been found to be particularly useful. The diluting solution must be isotonic so as to prevent hemolysis which has been found to cause false positive results. The diluting solution is preferably buffered (e.g., phosphate or tris-(hydroxymethyl)-amino-methane buffers, c.f. the examples which follow). The ingredients of the diluting solution (such as additional ingredients of the diluting solution (such as additional salts, e.g., sodium chloride) to obtain optional results for a given assay will be well within the ordinary skill in the art.

The parameters of the actual indirect, solid-phase immunoassay techniques that can be used in the present invention likewise are well within the ordinary skill in the art. In particular, the current state of the art teaches allowable and preferred sample volumes, incubation times and temperatures, available labels for the second antibody ($Ab_2^*$) and monitoring methods therefor, techniques for separating the solid-phase at various steps during the procedure, and techniques for correlating assay results to standard values. Further, various types of solid-phase forms of the viral antigen (Ag) are available in the art, including antigen immobilized on various carriers such as by physical adsorption or chemical coupling.

The present invention will now be illustrated, but is not intended to be limited, by the following examples.

| TABLE OF CONTENTS FOR EXAMPLES | |
|---|---|
| Example No. | |
| 1 | Preparation of soluble cytomegalovirus (CMV) antigen |
| 2 | Preparation of soluble Rubella antigen |
| 3 | Preparation of immobilized (coated tube) CMV antigen |
| 4 | Preparation of immobilized (coated tube) Rubella antigen |
| 5 | Preparation of radiolabeled ($^{125}$I) rabbit anti-human IgG |
| 6 | Radioimmunoassay for CMV antibody in finger prick whole human blood |
| 7 | Radioimmunoassay for Rubella antibody in finger prick whole human blood |
| 8 | Radioimmunoassay for CMV and Rubella antibodies in anticoagulant human blood |
| 9 | Enzyme immunoassay for CMV and Rubella antibodies in whole human blood |

EXAMPLE 1

Preparation of Soluble Cytomegalovirus (CMV) Antigen

Human primary embryonic fibroblasts were grown as monolayers in roller bottles containing minimum essential medium and 10% fetal calf serum (Grand Island Biological Company, New York, N.Y., U.S.A.). The cells were infected with CMV AD-169 strain (American Type Culture Collection, Rockville, Md., U.S.A.) at multiplicity of infection of 1 plaque forming unit (pfu) per cell. At the completion of the cytopathic effect, each roller bottle was washed with phosphate buffered saline (PBS) containing 0.8% sodium chloride, 0.02% potassium chloride, 0.115% dibasic sodium phosphate ($Na_2HPO_4$-$12H_2O$) and 0.02% monobasic potassium phosphate ($KH_2PO_4$) and the cells were scraped off the glass with glass beads, followed by pellet formation by centrifugation at $300 \times g$ for 10 minutes. The supernatant liquid was removed and the precipitated pellet of the cells was resuspended in 10 milliliters (ml) of glycine buffer (containing 0.85% sodium chloride and 0.05 M glycine; pH adjusted to 9.0 by means of sodium hydroxide). The suspension of the cells was sonicated for 2 minutes and allowed to stand overnight at 4° C. The suspension was clarified by centrifugation at $7700 \times g$ for 20 minutes and the released virions were pelletted at $100,000 \times g$ for 30 minutes, the soluble antigen remaining in the supernatant solution. This soluble antigen was stored at $-70°$ C.

EXAMPLE 2

Preparation of Rubella Antigen

Baby hamster kidney-21-C13 cells (Flow Laboratories, Scotland) were grown in roller bottles containing Dulbeco's modified essential medium (DMEM) and 10% fetal calf serum (Grand Island Biological Co.) and infected with Rubella virus M-33 strain (American Type Culture Collection). Starting 48 hours after the infection, the bottles were harvested daily for a week. Cell debris was removed by lowspeed centrifugation. Viral antigen was pelleted by centrifugation at $50,000 \times g$ for one hour through a cushion of 20% weight per weight of sucrose in TNE buffer [containing 20 millimolar (mM) tris-(hydroxymethyl)aminomethane, 100 mM sodium chloride and 1 mM ethylenediamine tetracetic acid; pH 7.4]. The pellet thus formed was resuspended in TNE buffer and the suspension was sonicated until clear. The resuspended pellets were further purified in a 20-60% w/w sucrose gradient in TNE buffer by centrifuging at 38,000 rpm for two hours. The viral band obtained was aspirated and dialyzed to four hours at 4° C. against glycine buffered saline, pH 9 (described in Example 1). Thereafter glycerol was added to a final concentration of 5%. This Rubella antigen suspension was stored frozen at $-70°$ C.

EXAMPLE 3

Preparation of Immobilized (Coated Tube) CMV Antigen

The CMV soluble antigen obtained in Example 1 was diluted with glycine buffer (described in Example 1) to a concentration of 100-150 micrograms per milliliter ($\mu g/ml$) of protein and a complement fixation titer of $\frac{1}{4}$-$\frac{1}{8}$. Aliquots (0.2 ml) of this solution were accurately and carefully pipetted into the bottom of separate $12 \times 75$ mm polystyrene test tubes (from Ultraplast, Tel-Aviv, Israel) and the test tubes were incubated at 4° C. for 16 hours. At the end of the incubation, the liquid remaining in the test tubes was removed, the test tubes were dried in an air stream, sealed with parafilm (Americal Can Company, Conn., U.S.A.) and stored at 4° C.

EXAMPLE 4

Preparation of Immobilized (Coated Tube) Rubella Antigen

The Rubella antigen obtained in Example 2 was diluted with glycine buffer (described in Example 1) to a concentration of about 10-15 μg/ml of protein and an RIA titer of about 1:32. Aliquots (0.2 ml) of this solution were accurately and carefully pipetted into the bottom of separate 12×75 mm polystyrene test tubes (from Ultraplast, Tel Aviv, Israel) and the test tubes were incubated at 4° C. for 16 hours. At the end of the incubation, the liquid remaining in the test tube was removed. The fixed antigen was inactivated by adding aliquots (0.2 ml) of 50% methanol diluted in TBS buffer (50 mM tris-(hydroxymethyl)-amino-methane, 0.85% sodium chloride) and incubating 5 minutes at room temperature. At the end of the incubation, the methanol was removed, the test tubes were dried in an air stream, sealed with parafilm and stored at 4° C.

EXAMPLE 5

Preparation of Radiolabeled ($^{125}I$) Rabbit Anti-human IgG

The IgG fraction of rabbit anti-human IgG serum was obtained by passing the serum through a DEAE-cellulose column (DE-52, Whatman Ltd., England) equilibrated with 0.015 M potassium phosphate buffer, pH 8.0. The IgG fraction thus obtained was radioactively labeled with $^{125}I$ by iodination in accordance with the chloramine T method described by Hutchinson and Zeigler, *Applied Microbiology*, December 1974, pp. 935-942.

EXAMPLE 6

Radioimmunoassay for CMV Antibody in Finger Prick Whole Human Blood

Approximately 10 microliters (μl) of finger prick blood were diluted with 0.5 ml PBS (described in Example 1) containing 1% bovine serum albumin (approximately a 1:50 dilution). A 0.2 ml aliquot of the diluted sample was added to a CMV antigen coated tube (prepared as in Example 3) and incubated 1 hour at 37° C. After aspirating the sample by vacuum, the tube was washed twice with approximately 3 ml PBS. A 0.2 ml volume of $^{125}I$-anti-human IgG (300,000 counts per minute; prepared as in Example 5) in PBS containing 1% bovine serum albumin was added to the tube and incubated 1 hour at 37° C. After aspirating the liquid by vacuum, the tube was washed twice with approximately 3 ml PBS. The radioactivity remaining in the tube was measured in a gamma-counter.

The procedure was repeated on other finger prick blood samples and parallel assays were conducted on serum samples from the same patients (diluted 1:100 in PBS containing 1% bovine serum albumin). The results were as follows:

| Sample No. | Counts per minute | |
|---|---|---|
| | Serum | Whole Blood |
| 1 | 814 | 655 |
| 2 | 6270 | 6265 |
| 3 | 6119 | 6456 |
| 4 | 2024 | 2325 |
| 5 | 3419 | 3252 |

EXAMPLE 7

Radioimmunoassay for Rubella Antibody in Finger Prick Whole Human Blood

Approximately 10 μl of finger prick blood were diluted with 0.5 ml TBS (50 mM tris-(hydroxymethyl)aminomethane, 0.85% sodium chloride, pH 6.5) containing 1% bovine serum albumin and 0.05% Tween 20 (polyethylene sorbitan monolaurate, J. T. Baker, N.J., U.S.A.). A 0.2 ml aliquot of the diluted sample (approximately a 1:50 dilution) was added to a Rubella antigen coated tube (prepared as in Example 4) and incubated 1 hour at 37° C. After aspirating the sample by vacuum, the tube was washed twice with TBS containing 0.05% Tween 20. A 0.2 ml volume of $^{125}I$-anti-human IgG (300,000 counts per minute) in TBS containing 1% bovine serum albumin and 0.05% Tween 20 was added to the tube and incubated 1 hour at 37° C. After aspirating the liquid by vacuum, the tube was washed twice with TBS containing 0.05% Tween 20. The radioactivity remaining in the tube was measured in a gamma-counter.

The procedure was repeated on other finger prick blood samples and parallel assays were conducted on serum samples from the same patients (diluted 1:100 in TBS containing 1% bovine serum albumin and 0.05% Tween 20). The results were as follows:

| Sample No. | Counts per minute | |
|---|---|---|
| | Serum | Whole Blood |
| 1 | 1177 | 1175 |
| 2 | 5949 | 5481 |
| 3 | 6700 | 6430 |
| 4 | 5316 | 5664 |
| 5 | 3195 | 3375 |

EXAMPLE 8

Radioimmunoassay for CMV and Rubella Antibodies in Anticoagulant Human Blood

The assays described in Examples 6 and 7 were repeated using, in place of finger prick whole human blood, blood taken from a vein mixed with an anticoagulant (citrate). Before taking a sample of the anticoagulant blood for an assay the blood was mixed to obtain a homogeneous distribution of red blood cells. The results are as follows:

| Sample No. | Counts per minute | |
|---|---|---|
| | Serum | Blood |
| CMV Antibody Assay | | |
| 1 | 789 | 703 |
| 2 | 2185 | 1985 |
| 3 | 6520 | 6318 |
| Rubella Antibody Assay | | |
| 1 | 609 | 625 |
| 2 | 6812 | 6425 |
| 3 | 8764 | 8060 |
| 4 | 5149 | 5271 |

EXAMPLE 9

Enzyme Immunoassay for CMV and Rubella Antibodies in Whole Human Blood

Approximately 10 μl of finger prick blood was diluted with 0.5 ml PBS (described in Example 2) containing 0.05% Tween 20 (J. T. Baker, N.J., U.S.A.). A 0.2 ml aliquot of the diluted sample (approximately a 1:50 dilution) was added to tubes coated with either CMV antigen or Rubella antigen (Examples 3 and 4), depending on which antibody was to be detected, and incubated 90 minutes at 37° C. After aspirating the sample by vacuum, the tube was washed twice with 3 ml PBS containing 0.05% Tween 20. A 0.2 ml volume of anti-human IgG labeled with the enzyme alkaline phosphatase (obtained from Miles-Yeda, Rehovot, Israel) in PBS containing 0.05% Tween 20 was added to the tube and incubated 90 minutes at 37° C. After aspirating the liquid by vacuum, the tube was washed twice with approximately 3 ml PBS containing 0.05% Tween 20. A 0.5 ml volume of enzyme substrate solution (constituting per liter of solution, 1 gram (g) 4-nitrophenyl phosphate, 97 ml diethanolamine, 0.2 g sodium azide, and hydrochloric acid to give pH 9.8) was added to the tube and incubated 30 minutes at 37° C. The optical density of the solution in the tube was measured at 435 nanometers (nm).

The procedure was repeated on other finger prick blood samples and parallel assays were conducted on serum samples from the same patients (diluted 1:100 in PBS containing 0.05% Tween 20). The results were as follows:

| Sample No. | O.D. at 435 nm | |
|---|---|---|
| | Serum | Whole Blood |
| CMV Antibody Assay | | |
| 1 | 0.241 | 0.288 |
| 2 | 0.931 | 0.910 |
| 3 | 2.680 | 2.610 |
| Rubella Antibody Assay | | |
| 1 | 0.593 | 0.661 |
| 2 | 0.849 | 0.784 |

Thus, the examples demonstrate that the present invention provides results in assaying whole blood samples not significantly different from those obtained in assaying serum samples.

What is claimed is:

1. In an immunoassay method for the detection of an antibody (Ab$_1$) to a viral antigen (Ag) in human blood wherein (a) a test sample is incubated with a solid-phase form of Ag whereby any Ab$_1$ present in the test sample becomes bound to said solid phase Ag,
    (b) the resulting solid-phase Ag-Ab$_1$ complexes are separated from the test sample,
    (c) a label-incorporated form of an antibody to Ab$_1$ (Ab$_2$*) is contacted with the separated, solid-phase Ag-Ab$_1$ complexes;
    (d) the resulting solid-phase Ag-Ab$_1$-Ab$_2$* complexes are separated from excess Ab$_2$*, and
    (e) the amount of said label in the separated, solid-phase Ag-Ab$_1$-Ab$_2$* complexes is measured as a function of the presence of Ab$_1$ in said test sample, the improvement which comprises employing as said test sample a whole human blood sample diluted at least 1:20 by volume with an isotonic aqueous solution, such dilution being less than that at which analytically significant concentrations of said antibody (Ab$_1$) in the undiluted test sample cannot be detected reproducibly.

2. The method of claim 1 wherein said whole human blood sample is diluted about 1:50 by volume with said isotonic aqueous solution.

3. The method of claim 1 or 2 wherein said isotonic aqueous solution comprises a buffer.

4. The method of claim 3 wherein said buffer is a phosphate buffer.

5. The method of claim 3 wherein said buffer is a tris-(hydroxymethyl)-aminomethane buffer.

6. The method of claim 1 wherein said whole human blood sample is obtained by a finger prick.

7. The method of claim 1 wherein Ag is cytomegalovirus antigen.

8. The method of claim 1 wherein Ag is Rubella antigen.

9. The method of claim 7 or 8 wherein Ab$_1$ is an IgG antibody and Ab$_2$* is a labeled form of anti-IgG.

10. The method of claim 7 or 8 wherein said label is a radioactive substance.

11. The method of claim 7 or 8 wherein said label is an enzyme.

* * * * *